United States Patent
Montagnier

(10) Patent No.: US 9,580,758 B2
(45) Date of Patent: Feb. 28, 2017

(54) SYSTEM AND METHOD FOR THE DETECTION AND TREATMENT OF INFECTION BY A MICROBIAL AGENT ASSOCIATED WITH HIV INFECTION

(71) Applicant: Luc Montagnier, New York, NY (US)

(72) Inventor: Luc Montagnier, New York, NY (US)

( * ) Notice: Subject to any disclaimer, the term of this patent is extended or adjusted under 35 U.S.C. 154(b) by 123 days.

(21) Appl. No.: 14/537,111

(22) Filed: Nov. 10, 2014

(65) Prior Publication Data

US 2015/0132343 A1    May 14, 2015

Related U.S. Application Data

(60) Provisional application No. 61/903,182, filed on Nov. 12, 2013.

(51) Int. Cl.
| | | |
|---|---|---|
| C12Q 1/68 | (2006.01) |
| A61K 31/65 | (2006.01) |
| A61K 31/496 | (2006.01) |
| A61K 31/00 | (2006.01) |
| C07H 21/02 | (2006.01) |

(52) U.S. Cl.
CPC .............. *C12Q 1/689* (2013.01); *A61K 31/00* (2013.01); *A61K 31/496* (2013.01); *A61K 31/65* (2013.01)

(58) Field of Classification Search
CPC ...................................... C12Q 1/689
See application file for complete search history.

(56) References Cited

U.S. PATENT DOCUMENTS

| | | |
|---|---|---|
| 4,167,583 A | 9/1979 | Knott et al. |
| 4,956,278 A | 9/1990 | Hart et al. |
| 5,399,485 A | 3/1995 | Regnery et al. |
| 5,549,898 A | 8/1996 | McGuire et al. |
| 5,644,047 A | 7/1997 | Anderson et al. |
| 5,665,772 A | 9/1997 | Cottens et al. |
| 5,693,776 A | 12/1997 | Anderson et al. |
| 5,736,347 A | 4/1998 | Anderson et al. |
| 5,763,239 A | 6/1998 | Short et al. |
| 5,795,563 A | 8/1998 | Kallick |
| 5,869,335 A | 2/1999 | Munderloh et al. |
| 5,912,253 A | 6/1999 | Cottens et al. |
| 5,972,309 A | 10/1999 | Kallick |
| 5,976,791 A | 11/1999 | Mabilat et al. |
| 5,985,890 A | 11/1999 | Cottens et al. |
| 5,994,072 A | 11/1999 | Lam et al. |
| 6,001,574 A | 12/1999 | Short et al. |
| 6,015,691 A | 1/2000 | Walker et al. |
| 6,168,915 B1 | 1/2001 | Scholl et al. |
| 6,200,985 B1 | 3/2001 | Cottens et al. |
| 6,280,926 B1 | 8/2001 | Short |
| 6,280,928 B1 | 8/2001 | Scholl et al. |
| 6,306,582 B1 | 10/2001 | Scholl et al. |
| 6,376,172 B1 | 4/2002 | Scholl et al. |
| 6,406,842 B2 | 6/2002 | Scholl et al. |
| 6,406,887 B1 | 6/2002 | Anderson et al. |
| 6,432,649 B1 | 8/2002 | Stich et al. |
| 6,440,990 B1 | 8/2002 | Cottens et al. |
| 6,444,426 B1 | 9/2002 | Short et al. |
| 6,472,206 B1 | 10/2002 | Scholl et al. |
| 6,482,415 B1 | 11/2002 | Ching et al. |
| 6,495,316 B1 | 12/2002 | Scholl et al. |
| 6,528,249 B1 | 3/2003 | Short |
| 6,551,795 B1 | 4/2003 | Rubenfield et al. |
| 6,573,080 B2 | 6/2003 | Scholl et al. |
| 6,632,600 B1 | 10/2003 | Short |
| 6,677,115 B2 | 1/2004 | Short |
| 6,699,654 B1 | 3/2004 | McLeod et al. |
| 6,699,674 B2 | 3/2004 | Ching et al. |
| 6,737,237 B1 | 5/2004 | McLeod et al. |
| 6,790,605 B1 | 9/2004 | Short |
| 6,822,084 B1 | 11/2004 | Pompejus et al. |
| 6,849,395 B2 | 2/2005 | Short |
| 6,852,546 B1 | 2/2005 | Brown |
| 6,875,600 B2 | 4/2005 | Scholl et al. |
| 6,887,688 B2 | 5/2005 | Lagarias et al. |
| 6,887,989 B2 | 5/2005 | Simard et al. |
| 6,936,432 B2 | 8/2005 | Gopalan et al. |
| 6,939,549 B2 | 9/2005 | de la Fuente et al. |
| 6,946,291 B2 | 9/2005 | Scholl et al. |
| 6,960,465 B1 | 11/2005 | Papoutsakis et al. |
| 6,964,868 B1 | 11/2005 | Williams et al. |
| 6,979,451 B1 | 12/2005 | de la Fuente et al. |
| 7,018,793 B1 | 3/2006 | Short |
| 7,033,781 B1 | 4/2006 | Short |
| 7,033,806 B2 | 4/2006 | Lagarias et al. |
| 7,186,561 B2 | 3/2007 | da Costa e Silva et al. |
| 7,214,509 B2 | 5/2007 | Schnoor et al. |
| 7,238,347 B2 | 7/2007 | Chang et al. |
| 7,241,867 B2 | 7/2007 | Bakaletz et al. |
| 7,261,887 B2 | 8/2007 | Chang et al. |
| 7,309,601 B2 | 12/2007 | Perez Esteban et al. |
| 7,329,503 B2 | 2/2008 | Ching et al. |
| 7,335,477 B2 | 2/2008 | Ching et al. |
| 7,341,829 B2 | 3/2008 | Scholl et al. |
| 7,361,504 B2 | 4/2008 | Munderloh |
| 7,371,821 B2 | 5/2008 | Ching et al. |
| 7,390,626 B2 | 6/2008 | Vojdani |
| 7,435,588 B2 | 10/2008 | Huang et al. |
| 7,442,508 B2 | 10/2008 | Scholl et al. |
| 7,504,384 B2 | 3/2009 | Yedgar et al. |
| 7,531,345 B2 | 5/2009 | Stephanopoulos et al. |
| 7,538,206 B2 | 5/2009 | Cole |
| 7,560,539 B2 | 7/2009 | Weaver et al. |
| 7,563,603 B2 | 7/2009 | Metz et al. |

(Continued)

FOREIGN PATENT DOCUMENTS

WO    WO2007137255 A2    11/2007

*Primary Examiner* — Teresa Strzelecka
(74) *Attorney, Agent, or Firm* — Steven M. Hoffberg Esq.; Ostrolenk Faber LLP

(57) ABSTRACT

A method of treating a patient, comprising administering at least one antibiotic, e.g., doxycycline and ciprofloxacin, sufficient to substantially treat an intracellular bacterial organism present in at least erythrocytes, e.g., over a course of at least two weeks; and subsequently administering at least one immunostimulant, e.g., which directly or indirectly increases levels of immunostimulatory cytokines in the patient, and at least one antioxidant, e.g., glutathione, to effectively treat a coinfection of the patient with a virus. The intracellular bacterial organism may be a rickettsiales-like organism, and the virus may be HIV.

19 Claims, 3 Drawing Sheets

(56) References Cited

U.S. PATENT DOCUMENTS

| | | |
|---|---|---|
| 7,563,604 B2 | 7/2009 | Metz et al. |
| 7,563,605 B2 | 7/2009 | Metz et al. |
| 7,601,522 B2 | 10/2009 | Weaver et al. |
| 7,608,753 B2 | 10/2009 | Metz et al. |
| 7,611,874 B2 | 11/2009 | Metz et al. |
| 7,611,875 B2 | 11/2009 | Metz et al. |
| 7,611,876 B2 | 11/2009 | Metz et al. |
| 7,626,009 B2 | 12/2009 | Weaver et al. |
| 7,629,450 B2 | 12/2009 | Weaver et al. |
| 7,635,481 B2 | 12/2009 | Hu et al. |
| 7,638,130 B2 | 12/2009 | Ching et al. |
| 7,638,282 B2 | 12/2009 | Bakaletz et al. |
| 7,638,315 B2 | 12/2009 | Metz et al. |
| 7,642,074 B2 | 1/2010 | Metz et al. |
| 7,645,597 B2 | 1/2010 | Metz et al. |
| 7,645,598 B2 | 1/2010 | Metz et al. |
| 7,662,597 B2 | 2/2010 | Metz et al. |
| 7,667,099 B2 | 2/2010 | Osteryoung et al. |
| 7,695,834 B1 | 4/2010 | Borole |
| 7,759,062 B2 | 7/2010 | Allawi et al. |
| 7,790,184 B2 | 9/2010 | Kranz |
| 7,799,564 B2 | 9/2010 | Weaver et al. |
| 7,803,620 B2 | 9/2010 | Weaver et al. |
| 7,803,765 B2 | 9/2010 | Watt et al. |
| 7,811,583 B2 | 10/2010 | Kirke et al. |
| 7,816,086 B2 | 10/2010 | Bakaletz et al. |
| 7,816,505 B2 | 10/2010 | Metz et al. |
| 7,824,875 B2 | 11/2010 | Ching et al. |
| 7,824,909 B2 | 11/2010 | Ching et al. |
| 7,838,287 B2 | 11/2010 | Goldsmith et al. |
| 7,842,296 B2 | 11/2010 | Simard et al. |
| 7,846,675 B2 | 12/2010 | Ching et al. |
| 7,847,077 B2 | 12/2010 | Metz et al. |
| 7,858,100 B2 | 12/2010 | Nylund |
| 7,879,608 B2 | 2/2011 | Weaver et al. |
| 7,888,491 B2 | 2/2011 | Rikihisa et al. |
| 7,897,392 B2 | 3/2011 | Weaver et al. |
| 7,897,393 B2 | 3/2011 | Weaver et al. |
| 7,902,427 B2 | 3/2011 | Weaver et al. |
| 7,906,706 B2 | 3/2011 | Weaver et al. |
| 7,939,716 B2 | 5/2011 | Weaver et al. |
| 7,943,363 B2 | 5/2011 | Blanchard et al. |
| 7,998,490 B2 | 8/2011 | Bakaletz et al. |
| 8,008,459 B2 | 8/2011 | Goldsmith et al. |
| 8,012,725 B2 | 9/2011 | Sturmer et al. |
| 8,029,804 B2 | 10/2011 | Ching et al. |
| 8,110,672 B2 | 2/2012 | Stephanopoulos et al. |
| 8,142,787 B2 | 3/2012 | Ching et al. |
| 8,142,997 B2 | 3/2012 | Scholl et al. |
| 8,192,854 B2 | 6/2012 | Borole |
| 8,206,908 B2 | 6/2012 | Frutos et al. |
| 8,236,494 B2 | 8/2012 | Bakaletz et al. |
| 8,283,114 B2 | 10/2012 | Bakaletz et al. |
| 8,287,876 B2 | 10/2012 | Ching et al. |
| 8,293,879 B2 | 10/2012 | Brown |
| 8,303,966 B2 | 11/2012 | Lin et al. |
| 8,318,915 B2 | 11/2012 | Anda Fernandez et al. |
| 8,354,232 B2 | 1/2013 | Allawi et al. |
| 8,361,480 B2 | 1/2013 | Harrus et al. |
| 8,367,654 B2 | 2/2013 | Clark et al. |
| 8,404,475 B2 | 3/2013 | McSpadden Gardener et al. |
| 8,435,537 B2 | 5/2013 | De La Fuenta Garcia et al. |
| 8,445,195 B2 | 5/2013 | Fernandez et al. |
| 8,470,965 B2 | 6/2013 | Schmidt et al. |
| 8,476,011 B1 | 7/2013 | Short |
| 8,501,463 B2 | 8/2013 | Cox et al. |
| 8,563,257 B2 | 10/2013 | Kohn et al. |
| 8,591,880 B2 | 11/2013 | Chou et al. |
| 8,591,906 B2 | 11/2013 | McBride et al. |
| 8,597,513 B2 | 12/2013 | Borole et al. |
| 8,623,996 B2 | 1/2014 | Zaliha et al. |
| 8,628,807 B2 | 1/2014 | Van Dijk et al. |
| 8,628,917 B2 | 1/2014 | Bakaletz et al. |
| 8,652,773 B2 | 2/2014 | Bakaletz et al. |
| 8,710,179 B2 | 4/2014 | Mor et al. |
| 8,722,411 B2 | 5/2014 | Banai et al. |
| 8,735,122 B2 | 5/2014 | Henot et al. |
| 8,765,426 B2 | 7/2014 | Tao et al. |
| 8,771,940 B2 | 7/2014 | Andersen et al. |
| 8,784,828 B2 | 7/2014 | Rikihisa |
| 8,815,562 B2 | 8/2014 | Sherman et al. |
| 8,822,193 B2 | 9/2014 | Asolkar et al. |
| 8,828,673 B2 | 9/2014 | Scholl et al. |
| 8,828,681 B2 | 9/2014 | Bell, III et al. |
| 8,828,988 B2 | 9/2014 | Clark et al. |
| 8,859,259 B2 | 10/2014 | Rude |
| 8,859,281 B2 | 10/2014 | Bell, III et al. |
| 8,871,488 B2 | 10/2014 | Dauner et al. |
| 8,889,378 B2 | 11/2014 | Kranz |
| 8,926,981 B2 | 1/2015 | Brown |
| 8,927,691 B2 | 1/2015 | Khan |
| 8,956,873 B2 | 2/2015 | Bell, III et al. |
| 8,962,563 B2 | 2/2015 | Dockal et al. |
| 8,975,049 B2 | 3/2015 | Liao et al. |
| 8,986,962 B2 | 3/2015 | Contag |
| 9,018,167 B2 | 4/2015 | Dockal et al. |
| 9,023,612 B2 | 5/2015 | Bell, III et al. |
| 9,028,841 B2 | 5/2015 | Henn et al. |
| 9,029,637 B2 | 5/2015 | Papes et al. |
| 9,034,642 B2 | 5/2015 | Bakaletz et al. |
| 9,051,557 B2 | 6/2015 | Battles et al. |
| 9,056,899 B2 | 6/2015 | Collins et al. |
| 9,085,764 B2 | 7/2015 | Bell, III et al. |
| 9,096,893 B2 | 8/2015 | Allawi et al. |
| 9,113,636 B2 | 8/2015 | von Maltzahn et al. |
| 9,119,401 B2 | 9/2015 | Huang et al. |
| 9,133,525 B2 | 9/2015 | Montagnier |
| 9,137,975 B2 | 9/2015 | Bell, III et al. |
| 9,140,702 B2 | 9/2015 | McBride et al. |
| 9,145,542 B2 | 9/2015 | Liao et al. |
| 9,150,889 B2 | 10/2015 | Liao et al. |
| 9,193,965 B2 | 11/2015 | Liao et al. |
| 2001/0021501 A1 | 9/2001 | Scholl et al. |
| 2001/0034022 A1 | 10/2001 | Scholl et al. |
| 2001/0036628 A1 | 11/2001 | Scholl et al. |
| 2002/0006610 A1 | 1/2002 | Scholl et al. |
| 2002/0137891 A1 | 9/2002 | Hill et al. |
| 2002/0193564 A1 | 12/2002 | Hill et al. |
| 2003/0049841 A1 | 3/2003 | Short et al. |
| 2003/0073235 A1 | 4/2003 | Lagarias et al. |
| 2003/0087418 A1 | 5/2003 | Scholl et al. |
| 2003/0104379 A1 | 6/2003 | Lagarias et al. |
| 2003/0104440 A1 | 6/2003 | Short et al. |
| 2003/0124634 A1 | 7/2003 | Lam et al. |
| 2003/0129601 A1 | 7/2003 | Cole |
| 2003/0186352 A1 | 10/2003 | McLeod et al. |
| 2003/0203357 A1 | 10/2003 | Huang |
| 2003/0215796 A1 | 11/2003 | Scholl et al. |
| 2003/0228623 A1 | 12/2003 | Cantor et al. |
| 2004/0040054 A1 | 2/2004 | Silva et al. |
| 2004/0077090 A1 | 4/2004 | Short |
| 2004/0092467 A1 | 5/2004 | Chang et al. |
| 2004/0121322 A9 | 6/2004 | Cole |
| 2004/0139500 A1 | 7/2004 | Osteryoung et al. |
| 2004/0170965 A1 | 9/2004 | Scholl et al. |
| 2004/0197896 A1 | 10/2004 | Cole |
| 2004/0219525 A1 | 11/2004 | Haertel et al. |
| 2005/0054030 A1 | 3/2005 | Schnoor et al. |
| 2005/0124010 A1 | 6/2005 | Short et al. |
| 2005/0142113 A1 | 6/2005 | McLeod et al. |
| 2005/0221439 A1 | 10/2005 | Bakaletz et al. |
| 2005/0249749 A1 | 11/2005 | de la Fuente et al. |
| 2005/0255043 A1 | 11/2005 | Hnatowich et al. |
| 2005/0260229 A1 | 11/2005 | de la Fuente et al. |
| 2006/0009912 A1 | 1/2006 | Thijsen et al. |
| 2006/0018888 A1 | 1/2006 | Chang et al. |
| 2006/0051778 A1 | 3/2006 | Kallick |
| 2006/0078884 A1 | 4/2006 | Pompejus et al. |
| 2006/0079485 A1 | 4/2006 | Yedgar et al. |
| 2006/0084799 A1 | 4/2006 | Williams et al. |
| 2006/0088821 A1 | 4/2006 | Short |
| 2006/0094105 A1 | 5/2006 | Huang et al. |
| 2006/0099628 A1 | 5/2006 | Ching et al. |
| 2006/0111848 A1 | 5/2006 | Carlow et al. |

(56) References Cited

U.S. PATENT DOCUMENTS

| | | |
|---|---|---|
| 2006/0166319 A1 | 7/2006 | Chan et al. |
| 2006/0167228 A1 | 7/2006 | Esteban et al. |
| 2006/0183888 A1 | 8/2006 | Chan et al. |
| 2006/0188524 A1 | 8/2006 | Hu et al. |
| 2006/0189568 A1 | 8/2006 | Yedgar |
| 2006/0189569 A1 | 8/2006 | Yedgar et al. |
| 2006/0189570 A1 | 8/2006 | Yedgar |
| 2006/0189571 A1 | 8/2006 | Yedgar |
| 2006/0194267 A1 | 8/2006 | Vojdani |
| 2006/0246475 A1 | 11/2006 | Peterson et al. |
| 2006/0286667 A1 | 12/2006 | Scholl et al. |
| 2007/0009929 A1 | 1/2007 | Ching et al. |
| 2007/0009932 A1 | 1/2007 | Stephanopoulos et al. |
| 2007/0026488 A1 | 2/2007 | Targett et al. |
| 2007/0031832 A1 | 2/2007 | Watt et al. |
| 2007/0039069 A1 | 2/2007 | Rogers et al. |
| 2007/0059810 A1 | 3/2007 | Pompejus et al. |
| 2007/0065910 A1 | 3/2007 | Stephanopoulos et al. |
| 2007/0065939 A1 | 3/2007 | Huang et al. |
| 2007/0077576 A1 | 4/2007 | Pompejus et al. |
| 2007/0178505 A1 | 8/2007 | Fischer et al. |
| 2007/0184460 A1 | 8/2007 | Ching et al. |
| 2007/0264256 A1 | 11/2007 | Bakaletz et al. |
| 2008/0009046 A1 | 1/2008 | Sturmer et al. |
| 2008/0032313 A1 | 2/2008 | Kranz |
| 2008/0032382 A1 | 2/2008 | Schnoor et al. |
| 2008/0131870 A1 | 6/2008 | Allawi et al. |
| 2008/0182974 A1 | 7/2008 | Williams et al. |
| 2008/0187942 A1 | 8/2008 | Brown |
| 2008/0248473 A1 | 10/2008 | Fernandez et al. |
| 2008/0260763 A1 | 10/2008 | Felgner et al. |
| 2008/0279881 A1 | 11/2008 | Ching et al. |
| 2008/0279894 A1 | 11/2008 | Savage et al. |
| 2008/0311640 A1 | 12/2008 | Cox et al. |
| 2009/0081746 A1 | 3/2009 | Liao et al. |
| 2009/0092975 A1 | 4/2009 | Stratford |
| 2009/0098647 A1 | 4/2009 | Ching et al. |
| 2009/0111154 A1 | 4/2009 | Liao et al. |
| 2009/0123468 A1 | 5/2009 | Khan |
| 2009/0175902 A1 | 7/2009 | Lin et al. |
| 2009/0176214 A1 | 7/2009 | Ching et al. |
| 2009/0208478 A1 | 8/2009 | Khan |
| 2009/0220525 A1 | 9/2009 | Nylund |
| 2009/0253142 A1 | 10/2009 | Allawi et al. |
| 2009/0259026 A1 | 10/2009 | Tomlinson et al. |
| 2009/0285857 A1 | 11/2009 | Ching et al. |
| 2009/0286222 A1 | 11/2009 | Scholl et al. |
| 2009/0286954 A1 | 11/2009 | Williams et al. |
| 2009/0291858 A1 | 11/2009 | Andersen et al. |
| 2009/0301880 A1 | 12/2009 | Frutos et al. |
| 2009/0311722 A1 | 12/2009 | Ching et al. |
| 2009/0325177 A1 | 12/2009 | Kohn et al. |
| 2010/0028966 A1 | 2/2010 | Blanchard et al. |
| 2010/0029552 A1 | 2/2010 | Watt et al. |
| 2010/0035320 A1 | 2/2010 | Blanchard et al. |
| 2010/0062438 A1 | 3/2010 | Danchin |
| 2010/0081792 A1 | 4/2010 | Grant et al. |
| 2010/0092804 A1 | 4/2010 | Borole |
| 2010/0143964 A1 | 6/2010 | Mor et al. |
| 2010/0166771 A1 | 7/2010 | Bakaletz et al. |
| 2010/0173280 A1 | 7/2010 | Huang et al. |
| 2010/0183654 A1 | 7/2010 | McBride et al. |
| 2010/0200495 A1 | 8/2010 | Borole et al. |
| 2010/0203359 A1 | 8/2010 | Borole |
| 2010/0209986 A1 | 8/2010 | Liao et al. |
| 2010/0239613 A1 | 9/2010 | Harrus et al. |
| 2010/0252443 A1 | 10/2010 | Borole |
| 2010/0285488 A1 | 11/2010 | Allawi et al. |
| 2010/0297677 A1 | 11/2010 | Kranz |
| 2010/0310569 A1 | 12/2010 | Bakaletz et al. |
| 2010/0317014 A1 | 12/2010 | Eshoo et al. |
| 2010/0322903 A1 | 12/2010 | Collins et al. |
| 2010/0323391 A1 | 12/2010 | Montagnier et al. |
| 2011/0027774 A1 | 2/2011 | Montagnier |
| 2011/0045011 A1 | 2/2011 | Ching et al. |
| 2011/0076710 A1 | 3/2011 | Montagnier |
| 2011/0097354 A1 | 4/2011 | De La Fuenta Garcia et al. |
| 2011/0104696 A1 | 5/2011 | Anda Fernandez et al. |
| 2011/0123501 A1 | 5/2011 | Chou et al. |
| 2011/0135646 A1 | 6/2011 | Bakaletz et al. |
| 2011/0143358 A1 | 6/2011 | Sampath et al. |
| 2011/0160075 A1 | 6/2011 | Ching et al. |
| 2011/0165673 A1 | 7/2011 | Battles et al. |
| 2011/0177515 A1 | 7/2011 | Sampath et al. |
| 2011/0206630 A1 | 8/2011 | Rude |
| 2011/0212121 A1 | 9/2011 | Ching et al. |
| 2011/0212123 A1 | 9/2011 | Lin et al. |
| 2011/0212541 A1 | 9/2011 | Tyler et al. |
| 2011/0218118 A1 | 9/2011 | Watt et al. |
| 2011/0223599 A1 | 9/2011 | Eshoo et al. |
| 2011/0250222 A1 | 10/2011 | Greub et al. |
| 2011/0250660 A1 | 10/2011 | Liao et al. |
| 2011/0258915 A1 | 10/2011 | Subhadra |
| 2011/0262982 A1 | 10/2011 | Liao et al. |
| 2011/0269714 A1 | 11/2011 | Xiao et al. |
| 2011/0293570 A1 | 12/2011 | McSpadden Gardener et al. |
| 2011/0293624 A1 | 12/2011 | Bakaletz et al. |
| 2012/0024701 A1 | 2/2012 | Montagnier et al. |
| 2012/0058514 A1 | 3/2012 | Zaliha et al. |
| 2012/0058935 A1 | 3/2012 | Moir et al. |
| 2012/0107900 A1 | 5/2012 | Greiner et al. |
| 2012/0108569 A1 | 5/2012 | Clark et al. |
| 2012/0115819 A1 | 5/2012 | Clark et al. |
| 2012/0124898 A1 | 5/2012 | Contag |
| 2012/0129801 A1 | 5/2012 | Artacho et al. |
| 2012/0156735 A1 | 6/2012 | Dauner et al. |
| 2012/0171237 A1 | 7/2012 | Ching et al. |
| 2012/0184030 A1 | 7/2012 | Dermanovic et al. |
| 2012/0196276 A1 | 8/2012 | Scholl et al. |
| 2012/0196338 A1 | 8/2012 | Blanchard et al. |
| 2012/0208280 A1 | 8/2012 | Banai et al. |
| 2012/0231521 A1 | 9/2012 | Khan |
| 2012/0263736 A1 | 10/2012 | Hauser |
| 2012/0264637 A1 | 10/2012 | Wiener-Kronish et al. |
| 2012/0301433 A1 | 11/2012 | Lu et al. |
| 2012/0321647 A1 | 12/2012 | Breaker et al. |
| 2013/0017204 A1 | 1/2013 | Bakaletz et al. |
| 2013/0059312 A1 | 3/2013 | Brown |
| 2013/0078254 A1 | 3/2013 | Bakaletz et al. |
| 2013/0089879 A1 | 4/2013 | Kellermann et al. |
| 2013/0115244 A1 | 5/2013 | Lin et al. |
| 2013/0122041 A1 | 5/2013 | Harrus et al. |
| 2013/0130341 A1 | 5/2013 | Liao et al. |
| 2013/0143205 A1 | 6/2013 | Montagnier |
| 2013/0183758 A1 | 7/2013 | Bell et al. |
| 2013/0196939 A1 | 8/2013 | Montagnier |
| 2013/0217000 A1 | 8/2013 | Montagnier |
| 2013/0230857 A1 | 9/2013 | Gnirke et al. |
| 2013/0253303 A1 | 9/2013 | Bell et al. |
| 2013/0267429 A1 | 10/2013 | Gardner et al. |
| 2013/0288325 A1 | 10/2013 | Liao et al. |
| 2013/0302876 A9 | 11/2013 | Khan |
| 2013/0345178 A1 | 12/2013 | Clark et al. |
| 2013/0345249 A1 | 12/2013 | Debec et al. |
| 2014/0017268 A1 | 1/2014 | Gebhart et al. |
| 2014/0057259 A1 | 2/2014 | Allawi et al. |
| 2014/0113816 A1 | 4/2014 | Huang et al. |
| 2014/0113853 A1 | 4/2014 | Khan |
| 2014/0120107 A1 | 5/2014 | Bakaletz et al. |
| 2014/0120552 A1 | 5/2014 | Kohn et al. |
| 2014/0127221 A1 | 5/2014 | Bakaletz et al. |
| 2014/0127721 A1 | 5/2014 | McBride et al. |
| 2014/0141452 A1 | 5/2014 | Watt et al. |
| 2014/0147467 A1 | 5/2014 | Yanez Carcamo et al. |
| 2014/0162256 A1 | 6/2014 | Rikihisa |
| 2014/0179638 A1 | 6/2014 | Zhang et al. |
| 2014/0199281 A1 | 7/2014 | Henn et al. |
| 2014/0200149 A1 | 7/2014 | Andersen et al. |
| 2014/0234903 A1 | 8/2014 | Piel et al. |
| 2014/0248607 A1 | 9/2014 | Banai et al. |
| 2014/0249036 A1 | 9/2014 | Fry et al. |
| 2014/0249037 A1 | 9/2014 | Fry et al. |
| 2014/0273144 A1 | 9/2014 | Hawkins et al. |
| 2014/0273203 A1 | 9/2014 | Bell et al. |

(56) References Cited

U.S. PATENT DOCUMENTS

| | | |
|---|---|---|
| 2014/0274925 A1 | 9/2014 | Jin et al. |
| 2014/0287432 A1 | 9/2014 | Higuchi |
| 2014/0287961 A1 | 9/2014 | Andersen et al. |
| 2014/0302076 A1 | 10/2014 | Middelberg et al. |
| 2014/0308379 A1 | 10/2014 | Christofidou-Solomidou et al. |
| 2014/0331365 A1 | 11/2014 | Tyler et al. |
| 2014/0335512 A1 | 11/2014 | Moysey et al. |
| 2014/0349349 A1 | 11/2014 | Dauner et al. |
| 2014/0377857 A1 | 12/2014 | Liao et al. |
| 2015/0007359 A1 | 1/2015 | Bell et al. |
| 2015/0010937 A1 | 1/2015 | Bell et al. |
| 2015/0020239 A1 | 1/2015 | von Maltzahn et al. |
| 2015/0031016 A1 | 1/2015 | Scholl et al. |
| 2015/0050717 A1 | 2/2015 | Collins et al. |
| 2015/0064787 A1 | 3/2015 | Bell et al. |
| 2015/0132343 A1 | 5/2015 | Montagnier |
| 2015/0152391 A1 | 6/2015 | Bell et al. |
| 2015/0174226 A1 | 6/2015 | Carlyon |
| 2015/0216888 A1 | 8/2015 | Bellaire et al. |
| 2015/0218231 A1 | 8/2015 | Bakaletz et al. |
| 2015/0225687 A1 | 8/2015 | Bell et al. |
| 2015/0230478 A1 | 8/2015 | Vujanovic et al. |
| 2015/0250897 A1 | 9/2015 | Mattey et al. |
| 2015/0252320 A1 | 9/2015 | Battles et al. |
| 2015/0267175 A1 | 9/2015 | Bell et al. |
| 2015/0275182 A1 | 10/2015 | Bell et al. |
| 2015/0285798 A1 | 10/2015 | Jin et al. |
| 2015/0301042 A1 | 10/2015 | Brown |
| 2015/0313983 A1 | 11/2015 | Rikihisa et al. |
| 2015/0313992 A1 | 11/2015 | Bell et al. |
| 2015/0320050 A1 | 11/2015 | von Maltzahn et al. |
| 2015/0322492 A1 | 11/2015 | Huang et al. |
| 2015/0337363 A1 | 11/2015 | Andersen et al. |
| 2015/0342196 A1 | 12/2015 | von Maltzahn et al. |
| 2015/0361470 A1 | 12/2015 | Sherman et al. |
| 2015/0376656 A1 | 12/2015 | Liao et al. |
| 2015/0376724 A1 | 12/2015 | Montagnier |

Gel electrophoresis of the PCR amplified 400 bp band in HIV positive patients compared with two HIV negative individuals.
(56 degrees Celsius, with 50 cycles)

HIV negative patients with autism, Lyme disease, multiple sclerosis, and rheumatoid arthritis: no 400 bp band 400 bp sequence can be grown in vitro together with the Rickettsiales-like agent in the cell line HL60, and that it is also sensitive *in vitro* to treatment by chloram

SEQUENCE LISTING

<160> NUMBER OF SEQ ID NOS: 2

<210> SEQ ID NO 1
<211> LENGTH: 24
<212> TYPE: DNA
<213> ORGANISM: Artificial Sequence
<220> FEATURE:
<223> OTHER INFORMATION: PCR primer for Rickettsiales-like organism, 400 bp amplicon, Sense: pRICK 1

```
<400> SEQUENCE: 1
cctgagaaga gatttaagaa caaa                                              24

<210> SEQ ID NO 2
<211> LENGTH: 22
<212> TYPE: DNA
<213> ORGANISM: Artificial Sequence
<220> FEATURE:
<223> OTHER INFORMATION: PCR primer for Rickettsiales-like organism,
      400 bp amplicon, AntiSense: pRICK 1

<400> SEQUENCE: 2
ccatatactg cttctarytg ct                                                22
```

SYSTEM AND METHOD FOR THE DETECTION AND TREATMENT OF INFECTION BY A MICROBIAL AGENT ASSOCIATED WITH HIV INFECTION

CROSS REFERENCE TO RELATED APPLICATION

The present application claims benefit of priority from U.S. Patent Provisional Application No. 61/903,182, filed Nov. 12, 2013, the entirety of which is expressly incorporated herein by reference.

FIELD OF THE INVENTION

The present invention relates to the field of detection and treatment of microbial infection, and more particularly infection associated with HIV.

BACKGROUND OF THE INVENTION

This application incorporates by reference U.S. Provisional Application 61/716,123, filed Oct. 19, 2012; U.S. Provisional Application 61/591,111, filed Jan. 26, 2012, U.S. patent application Ser. No. 13/752,003, filed Jan. 28, 2013; U.S. Provisional Application Nos. 61/186,610; 61/358,282; 61/476,110; 61/476,545; Ser. Nos. 12/797,286; 13/168,367; 61/591,111; and PCT/US2010/038160.

Based on the hypothesis that AIDS is caused by a unique agent, the HIV retrovirus, antiretroviral (ARV) therapy including a combination of inhibitors of the viral enzymes, reverse transcriptase and of protease has been utilized in HIV infected patients with significant success worldwide. The viral multiplication as assessed by the number of viral RNA copies in blood has been reduced to almost zero, resulting in increase of CD4 T lymphocytes, the main target of the virus, and in prevention of the most deadly opportunistic infections.

However, interruption of this treatment leads to a rapid rebound of the virus, indicating that a reservoir of HIV persists unaffected by the treatment. In fact, viral DNA can be detected by sensitive methods (PCR) in the plasma and red blood cell (RBC) fraction of HIV infected patients under continuous ARV therapy (1). Up to now, there has been no existing test to further explore the status of HIV, after ARV therapy has made the viral RNA undetectable in the patient's blood.

A strong oxidative stress has been observed even at the early stage of HIV infection (2). This oxidative stress, as detectable by measurement of various blood parameters (3), is only partly reduced by the ARV treatment.

Oxidative stress is a potent inducer of lymphocyte activation, a status required for HIV integration and multiplication (2).

Oxidative stress is generated by bacterial infections and therefore there is a possibility that a specific bacterial or bacterial-like factor is a promoter of HIV multiplication.

Alpha-proteobacteria of the Order Rickettsiales have an obligate intracellular lifestyle, and have coevolved with their various eukaryotic hosts, resulting in small reductive genomes and strict dependency on host resources. A high portion of Rickettsiales genomes encodes for proteins involved in transport and secretion. Some rickettsiales are symbionts and others are pathogenic.

Acinetobacter is a bacteria of order gamma-proteobacteria, and is widespread in the environment and is known to cause human pathology, especially in immune-compromised individuals. Acinetobacter is not as a rule an intracellular parasite, and is known to form biofilms.

SUMMARY OF THE INVENTION

Microorganisms associated with HIV infection that are detectable in human red blood cells, but not in human leukocytes or other kinds of nucleated human cells. The identification and characterization of microorganisms associated with HIV infection is of interest for purposes of assessing risk of HIV infection or determining the status of an HIV infected patient, for assessing risk or status of opportunistic infections, and to evaluate modes of treatment for HIV infected subjects.

The present invention provides a new tool to give information to the clinician as to whether the residual virus is persisting indefinitely in the patient's body, or is progressively declining.

U.S. patent application Ser. No. 13/752,003 (Montagnier), US Pat. Pub. 2013/0196939, expressly incorporated herein by reference, describes some specific primers for the detection by PCR of certain DNA sequences present in red blood cells of HIV infected patients and in some HIV negative individuals of African origin or living in Africa. These sequences, respectively 237 and 213 base pair (bp) long, originate from human chromosomes 1 and 7, and seem to be associated with a microbial agent present in red blood cells, as shown by their sensitivity to antibiotic treatment, as discussed in Example 2.

A microbial agent was detected by PCR primers for 16S ribosomal DNA designed for Rickettsiales, and its 16S DNA amplicon had high sequence homology, about 90%, to some Rickettsiales (an alpha-proteobacteria) but was also close to the 16S DNA of the bacterium Acinetobacter (a gamma-proteobacteria). This organism was found in both normal and HIV infected individuals, but the human chromosome 1 and 7 sequences are only associated with the organism found in HIV-infected individuals and in the RBC of some HIV negative Africans. The organism is associated with, and likely within, the red blood cells, and the presence only in the cellular fraction and not in the plasma would tend to indicate that the organism is an obligate intracellular parasite. Because the organism is found in normal (healthy) individuals, it may be a symbiont. Based on these characteristics, it seems appropriate to consider the organism to be related to or within the rickettsiales, though full sequencing and formal taxonomy has not been completed. The relation of the 16S RNA to acinetobacter may have resulted from a horizontal transfer event, and thus does not necessarily represent a more global phylogenetic relationship.

The putative biology of the organism thus makes a rickettsiales classification, e.g. a mitochondria-like organism, more likely, though full identification is not yet available, and presumptive characteristics indicate that this organism is not a known *rickettsia* (a genus within rickettsiales).

Rickettsiales are obligate intracellular parasites. It is believed that such a lifestyle can cause a relatively rapid evolutionary divergence for closely phylogenetically related organisms due to host cell differences and selective pressures. The order displays broad phenotypic, antigenic, and genetic diversity, though the 16S RNA sequence is sufficiently conserved to be generally useful for phylogenetic classification.

In addition, the DNA polymerase of various organisms within the alpha-proteobacteria has characteristics of a reverse transcriptase, i.e., an RNA-dependent DNA polymerase, which in some cases permits acquisition and integration of foreign genes from RNA sequences. It is possible that this activity is relevant to the acquisition of the human chromosome 1 and 7 sequences by the organism. HIV also has a reverse transcriptase, and involvement of HIV in acquisition by the rickettsiales like organism of the human DNA sequences cannot be ruled out.

Based on PCR evidence, the Rickettsiales-like organism has been found to be present in RBC of the general population (normal) of Caucasian or African origin. However, the human chromosome 1 and 7 sequences are only found to be present in the RBC of HIV infected patients, being apparently associated with the Rickettsiales-like organism, since they are decreased at the same rate in patients receiving a strong antibiotic regimen.

Therefore, one aspect of the invention is the measurement of the human chromosome 1 and/or 7 sequences in patient red blood cells, which appears associated with HIV infection. Because this marker is independent of HIV antigens and particular genetic sequences, it can provide further information for patients where the HIV infection status is indeterminate from standard lab tests. However, since this marker is dependent on coinfection and/or antibiotic treatment status, and perhaps antiretroviral (ARV) therapy, it provides different information to a clinician.

According to one aspect of the invention, based on an understanding that the rickettsiales-like organism is likely responsible for generation of free radicals and oxidative stress, an antibiotic therapy is applied to substantially reduce a load of the organism, and thus also reduce the oxidative stress on the host cells. Antioxidants. Such as glutathione, ascorbic acid, polyphenols, tocopherol, carotenes, ubiquinone, etc., may be administered to bolster host antioxidant reserves. Subsequently, immunostimulant therapy is commenced, to bolster host reserves of glutathione, and to stimulate the host immune system.

For example, if, in an HIV-infected patient, the rickettsiales like organism associated with the human chromosome 1 and 7 sequences is cleared, and the patient is treated with concurrent ARV therapy to reduce HIV activity to undetectable levels, a cessation of the antibiotics may lead to a return of the rickettsiales-like organism. However, by following antibiotic therapy with administration of immunostimulants and antioxidants, an endogenous response to the organism may be induced to avoid pathological consequences of infection.

Immunostimulants include, for example: Cytokines: including IL-2, G-CSF, GM-CSF; Microbial fragments/toxins: beta-glucans, (Wagner, 1999); Osato Fermented *Papaya* Preparation (Osato Laboratories, Japan); Herbs: e.g., *Echinacea*, (Wagner, 1999), astragalus, garlic, *ginseng*, green tea, Guduchi (*Tinospora cordifolia*), maca, and Reishi mushrooms (*Ganoderma lucidum*), or extracts from them; Probiotics: *Lactobacillus* rhamnosus GG (Gill and Cross, 2002; Clancy, 2003); Antioxidant Vitamins: Ascorbic acid (Hughes, 2002; Allard et al., 1998); Animal Products: Propolis (bee gum), (Sforcin, 2007). See, Allard, J. P. et al. (1998). "Effects of vitamin E and C supplementation on oxidative stress and viral load in HIV-infected subjects," AIDS 12, pp. 1653-1659; Clancy, Robert (2003), "Immunobiotics and the probiotic evolution," FEMS Immunology and Medical Microbiology (August 18), Vol. 38(1), pp. 9-12; Cohen, Jonathan and William G. Powderly (2004). Infectious Diseases. 2nd ed., 2 vols. New York: Mosby, p. 1402; Dillon, Kenneth J. (1998). Healing Photons. Washington, D.C.: Scientia Press; Dillon, Kenneth J. (2003). Close-to-Nature Medicine. Washington, D.C.: Scientia Press; Dillon, Kenneth J. (2008). Intriguing Anomalies: An Introduction to Scientific Detective Work. Washington, D.C.: Scientia Press Garden of Life (www.gardenoflifeusa.com); Gill, Harsharnjit S. and Martin L. Cross (2002), "Probiotics and Immune Function," in Calder, Philip C., C. J. Field, and H. S. Gill. Nutrition and Immune Function. New York: CABI, pp. 251-272; Hughes, David A. (2002), "Antioxidant Vitamins and Immune Function," in Calder, Philip C., C. J. Field, and H. S. Gill. Nutrition and Immune Function. New York: CABI, pp. 171-191; Kuvibidila, Solo and B. Surendra Baliga (2002), "Role of Iron in Immunity and Infection," in Calder, Philip C., C. J. Field, and H. S. Gill. Nutrition and Immune Function. New York: CABI, pp. 209-228 Microminerals; Prasad, Ananda S. (2002), "Zinc, Infection and Immune Function," in Calder, Philip C., C. J. Field, and H. S. Gill. Nutrition and Immune Function. New York: CABI, pp. 193-207; Sforcin J M. (2007) "Propolis and the immune system: a review." Journal of Ethnopharmacology 113(1): 1-14; Ullman, Dana (2003), "Controlled Clinical Trials Evaluating the Homeopathic Treatment of People with Human Immunodeficiency Virus or Acquired Immune Deficiency Syndrome," The Journal of Alternative and Complementary Medicine, Vol. 9, No. 1, pp. 133-141; Wagner, Hildebert, ed. (1999). Immunomodulatory Agents from Plants. Boston: Birkhaeuser.

Therefore, one aspect of the technology is to apply an antibiotic therapy to clear the rickettsiales-like organism, in a patient having concurrent HIV infection, and then treat the patient with antioxidants and immunostimulants.

Assuming that the rickettsiales-like organism is not merely an incidental symbiont, but rather is a cofactor for HIV infection and progression of the disease to AIDS, the antibiotic regimen may also be therapeutic for the HIV-associated pathology (bit not for the HIV itself). While continuous antibiotic therapy is typically contraindicated, an immunostimulant therapy bolstered with antioxidant therapy may lead to persistent benefit to the patient.

Likewise, as the organism is identified and cultured, antibiotic sensitivity assays conducted and targeted therapy instituted with a narrow spectrum antibiotic rather than broad spectrum therapy. Such narrow spectrum antibiotics may tend to have a lesser effect on other microbes and therefore reduced incidence of antibiotic resistant strains.

Another aspect of the invention provides specific primers used to detect the organism. These 16S ribosomal primers are not specific for the human chromosome 1 and 7 fragments, and therefore can detect this organism in various human populations. Since the biology of this organism has not been fully studied, it may also be associated with other diseases or pathology, and identification of the organism is one step in determining its relationship to disease or human biology.

A separate set of primers has been found to amplify a sequence associated with this organism that selectively occurs in coinfection with HIV.

Because of its affinity for human red blood cells, one might assume that the organism has an oxidative metabolism and likely reliance on cellular glutathione and thioredoxin reductase and superoxide dismutase, etc., to detoxify the free radicals it produces. Likewise, the acquisition of human chromosome 1 and 7 sequences might indicate that the organism is found in erythroblasts and/or other erythropoietic cells, and perhaps other nucleated cells or platelets. Indeed, the rickettsiales-like organism may be a true symbiont for human RBCs, and provide a cellular maintenance function to, for example, increase lifespan. Alternately, this may be a chronic pathogen, which provides no significant host benefit.

It is believed that the organism is a cofactor for infection and/or pathogenicity of HIV. It is therefore another aspect to treat the microbial infection with antibiotics, which may be, for example, doxycyline and/or ciprofloxacin, given in traditional manner. Targeted antibiotics may also be employed based on antibiotic sensitivity assays.

Concurrent therapy with immunostimulants while infection is apparent and being treated with antibiotics is undesired, since each can consume antioxidants, and together cause a suppression of glutathione and shift in the host to a Th2 immune response pattern, instead of the desired Th1 response pattern. Thus, the preferred therapy treats the microbial organism with antibiotics prior to commencing immunostimulant therapy. While antioxidant therapy can be concurrent with both phases of the therapy, it is qualitatively more important during immunostimulant therapy to ensure a Th1 response pattern.

It is believed that these rickettsiales-like organisms produce an oxidative stress on the host, which in turn promotes HIV replication. It is therefore a further aspect of the technology to treat patients infected with this organism with an antioxidant therapy regimen, such as glutathione, alpha lipoic acid, ascorbic acid, polyphenols, CoQ, resveratrol, carotenes, tocopherols, tocotrienols, lycopene, etc. Preferably, the end result of antioxidant therapy is an increase in hepatic and/or erythrocyte glutathione reserves, either by direct administration of glutathione or indirect methods of increasing glutathione.

With an obligate intracellular lifestyle, Alpha-proteobacteria of the order Rickettsiales have inextricably coevolved with their various eukaryotic hosts, resulting in small, reductive genomes and strict dependency on host resources. Unsurprisingly, large portions of Rickettsiales genomes encode proteins involved in transport and secretion. (5) The rickettsiales-like organism may therefore be targeted through a unique or critical transport system, for example using a small-molecule therapeutic agent that has access to the cellular compartment of RBC.

BB31 DNA is from *Borrelia burgdorferi*;

EMK and ELL are DNA samples from African HIV negative individuals, positive for 213 and 237 bp human chromosomal sequences;

TITY and VIC are DNA from Caucasian HIV positive patients;

086 and 097 are DNA from African HIV positive patients;

CHA is DNA from an HIV positive Caucasian patient; and

Figure 3:
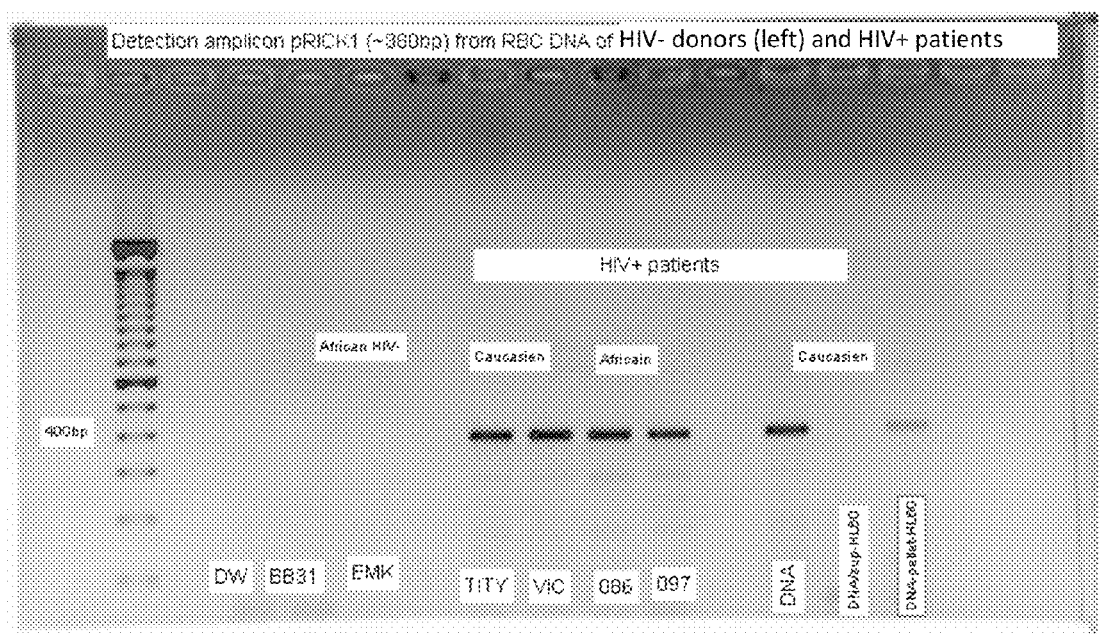
FIG. 3 shows gel electrophoresis using the same conditions as in FIGS. 1A and 1B, demonstrating that the 400 bp sequence can be grown in vitro together with the Rickettsiales-like agent in the cell line HL60, and that it is also sensitive in vitro to treatment by chloramphenicol.

RBC extract grown in HL60 cells, after centrifugation at 15 000 rpm, for 30 minutes (far right bands in FIG. 3); DNA was extracted from supernatant and pellet; Note that the 400 bp band is located in the pellet, confirming it belongs to a micro-organism.

DETAILED DESCRIPTION OF THE PREFERRED EMBODIMENTS

Example 1

One aspect of the present invention describes a set of new PCR primers for detecting a 400 bp DNA sequence uniquely present in the red blood cells of HIV infected patients, whatsoever their geographical location and their ethnic origin. This 400 bp DNA sequence has not been detected in the red blood cells of HIV negative individuals.

The 400 bp sequence has some sequence homology with the "Gypsy" retrotransposon sequence of human genomic DNA (e.g., 70-80%).

The sequences of the primers are the following:

```
1) pRICK 1 S
                                       SEQ ID NO: 001
   5'-CCT GAG AAG AGA TTT AAG AAC AAA 2) pRICK 1 AS
                                       SEQ ID NO: 002
   5'-CCA TAT ACT GCT TCT ARY TGC T
```

The optimal conditions for detecting the 400 bp amplicon by PCR in red blood cells are: annealing temperature of 56 degrees Celsius, with 50 cycles of amplification (up to about 70 cycles) in a thermocycler.

However, this sequence appears to be part of the human genome, as it is detected also by the same primers in a 99% homologous sequence located in the p region of human chromosome 1 (using BLAST against a human genome databank), a region distant from that of the 237 bp sequence (located in the q region), discussed in U.S. patent application Ser. No. 13/752,003 (Montagnier), US Pat. Pub. 2013/0196939, also located in human chromosome 1 (See Example 2).

Figure 1A:
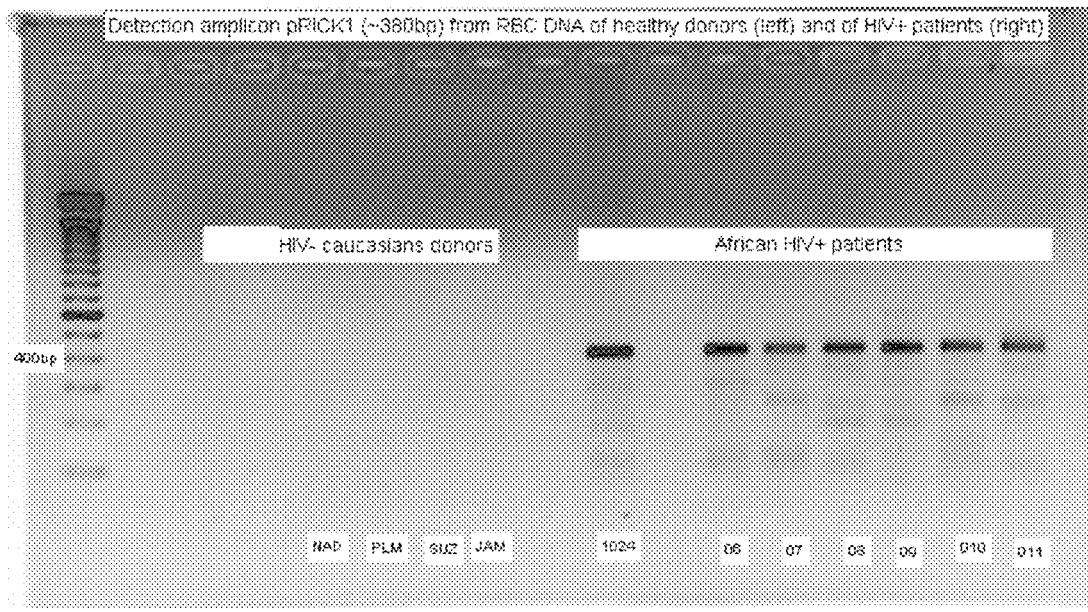
FIGS. 1A and 1B show gel electrophoresis of the PCR amplified 400 bp band using pRICK1 primer in HIV positive patients compared with two HIV negative individuals.
Figure 1B:
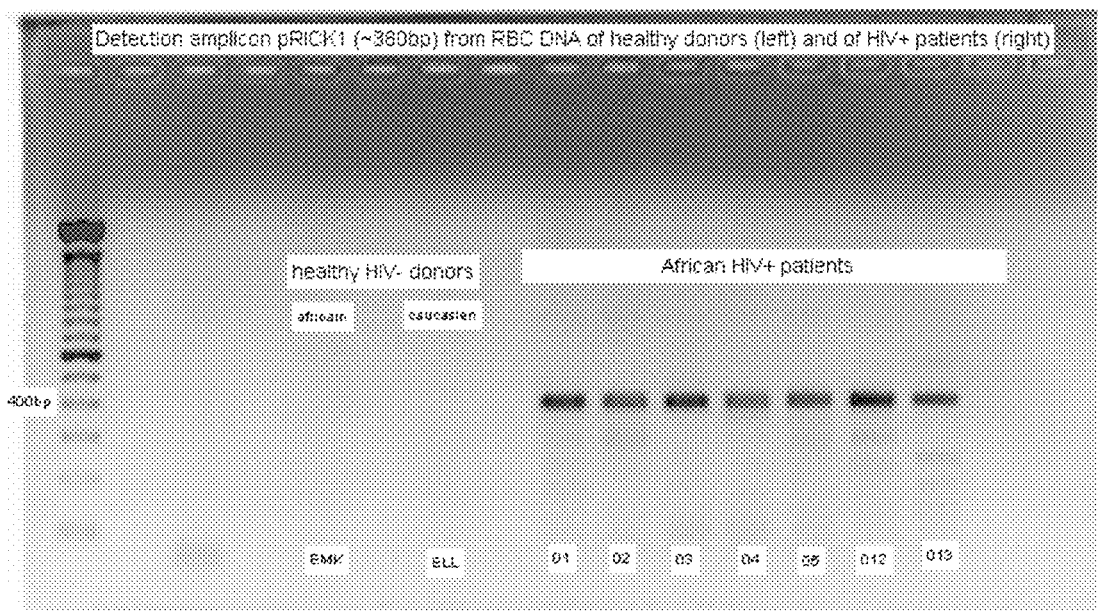

FIGS. 1A and 1B compare, on the left, several HIV negative individuals, and on right, several HIV positive patients: only the HIV positive patients show the characteristic 400 bp band detected by the new primers in the RBC DNA.

Red Blood Cells (RBC) were purified on a Ficoll gradient and DNA was extracted by a Qiagen kit according to the manufacturer's recommendations.

Figure 2A:
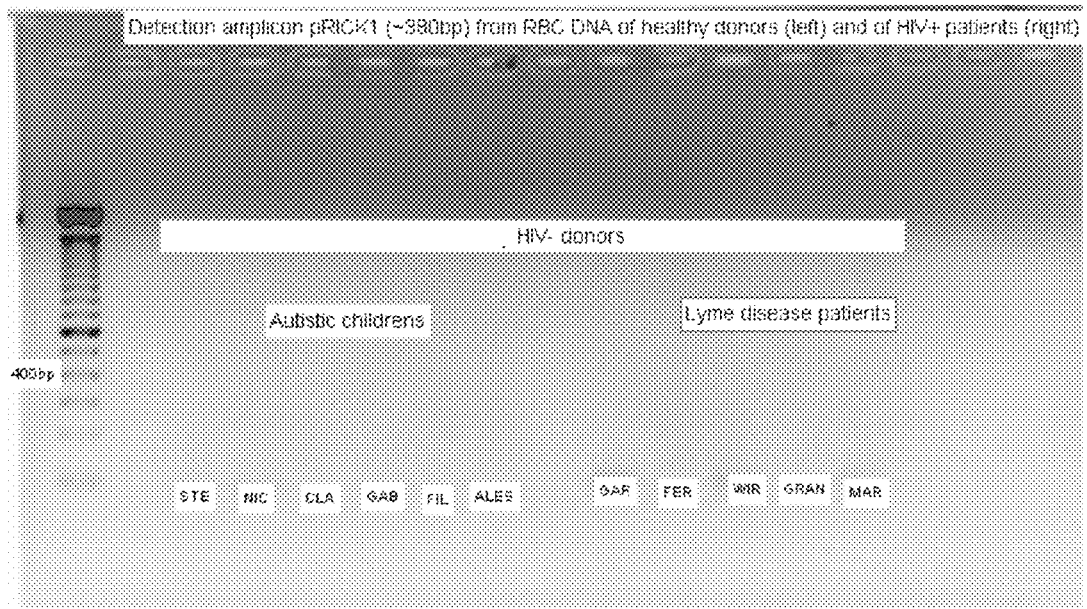
FIGS. 2A and 2B show gel electrophoresis using the same conditions as in FIGS. 1A and 1B on HIV negative patients with autism, Lyme disease, multiple sclerosis, and rheumatoid arthritis, showing no 400 bp band.
Figure 2B:
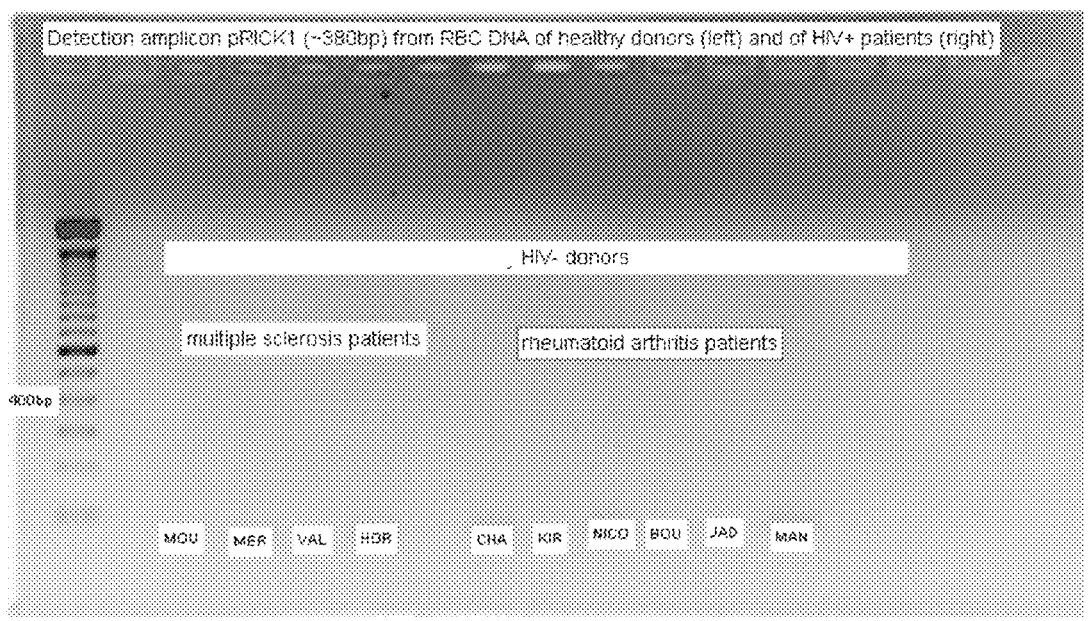

FIGS. 2A and 2B show negative results with the DNA of RBC from patients suffering from other diseases (autism, Lyme disease, multiple sclerosis, rheumatoid arthritis).

In the same experiment, the human genomic DNA was extracted from the leukocyte layer obtained from the same Ficoll gradient and, as expected, the sequence was detected by PCR in the DNA of all individuals, HIV positive and HIV negative.

Control PCR with the Beta-actin gene confirms the lack of this DNA in the RBC fraction, unlike in the genomic DNA contained in the leukocyte fraction, revealing that the RBC fraction was not generally contaminated with genomic DNA from nucleated cells in HIV infected patients, but that only some specific DNA sequences are incorporated in the RBC, associated with the microbial factor.

A test was also conducted seeking to determine whether the 400 bp sequence was present in the HIV genome. For this, we used a DNA plasmid including the full infectious HIV DNA genome (4). PCR analysis with the 400 bp primers indicates that this sequence was not part of the HIV genome.

In addition, primers for detection of a 194 bp fragment of the HIV LTR were also tested. Results were negative in the RBC fraction of HIV infected patients. (This finding is at variance with 2009 results reported in Reference (1), though the preferred antiretroviral therapy regimens have changed in the time between these studies).

By contrast, HIV DNA LTR was detected in plasma fractions from all HIV infected patients studied.

The significance of incorporation of some chromosomal DNA sequences in RBC remains to be determined, but it appears to serve as a reliable marker not present in normal individuals. This finding is of practical interest, showing for the first time that all HIV patients tested by the inventor harbor a non-HIV DNA marker, sensitive to antibiotic treatment. Note that the prokaryotic host for this non-HIV DNA marker also appears in normal individuals, and is antibiotic sensitive in both populations, but in HIV-infected individuals, the 400 bp marker is specifically present.

Latent HIV is known to be responsive to cellular redox potential, and is activated by oxidative conditions. Meanwhile, HIV replication is also associated with an oxidative burst, and maturation of the virions requires oxidative (disulfide crosslinking) conditions.

Rickettsiales are known to cause oxidative pathology in their respective hosts, and the related mitochondria are well known for their oxidative metabolism.

This prokaryotic organism is a putative cofactor that activates HIV in vivo, inducing viral replication and enhanced efficiency of infection.

According to one aspect of the invention, a treatment is provided for this prokaryotic organism, such as with doxycycline and ciprofloxacin for 2 weeks or more, in order to reduce at least the metabolic activity of the organism, if not its presence.

Note that during antibiotic treatment, the marker may not be reflective of HIV infection status, and therefore it is preferred that the use of the non-HIV DNA as a marker is assessed prior to antibiotic treatment. If the prokaryotic organism is not completely cleared through extended therapy (or possible reinfection), the marker returns, and therefore post-treatment assessment of the marker assesses both the presence of the HIV infection and the status of the microbial infection. Indeed, since the putative biology for the rickettsiales like organism is such that the presence of human chromosome 1 and 7 sequences are related to the bacteria and not directly dependent on HIV, and since the rickettsiales like organism associated with human chromosome 1 and 7 sequences is presumably independently infectious, it is anticipated that the presence of the rickettsiales like organism associated with human chromosome 1 and 7 sequences is not per se sufficient to determine whether a patient is infected with HIV.

As shown in FIG. 3, the 400 bp sequence can be grown in vitro together with the Rickettsiales-like agent in the cell line HL60. In addition it is also sensitive in vitro to treatment by chloramphenicol at a dose of 200 µg/ml.

FIGS. 1B and 3 indicate that 2 HIV negative individuals (EMK and ELL), in which the 213 bp and 237 bp chromosomal DNA sequences were present, lack the 400 bp sequence, a sequence which is therefore specific to HIV infected patients.

By way of example, and absent definitive proof, the etiology of the 400 bp sequence only in the HIV-infected individuals tested to date might, for example, be due to activity of an HIV-specific enzyme, e.g., HIV reverse transcriptase, acting on a cellular nucleic acid fragment (e.g., an RNA sequence corresponding to the Chromosome 1 DNA), which then gets incorporated, for example as a plasmid, within a commensal rickettsiales-like organism which is found in RBCs. Alternately, the rickettsiales-like organism with the 400 bp sequence is a stable organism, and it is this version that acts as a cofactor for HIV.

Further, the nucleic acids for this rickettsiales-like organism have not been fully sequenced for either HIV-infected or normal populations, and therefore it is not known whether the 400 bp fragment so far identified, is not part of a larger sequence of DNA which may be functional.

It is believed that the 400 bp sequence-containing organism is an HIV cofactor and the 400 bp sequence is part of, or associated with a functional sequence relating to viral replication and/or transmission. Given the biological burden of maintaining the 400 bp sequence and its associated sequences, it is likely that it provides some advantage to the rickettsiales-like organism in HIV infected individuals.

As a putative cofactor for HIV, the activity of this organism would increase the pathogenicity of HIV, for example due to NF-kappa B activation in the patient's cells, resulting in HIV replication. Consistent with this proposal, the rickettsiales-like organism is oxidative, and would induce an oxidative stress, a known activator of NF-kappa B.

The specificity of the 400 bp fragment as a marker for HIV infection (i.e., co-infection) suggests that it gives a selective advantage for the growth of the virus in HIV infected patients.

It is known that HIV infection causes an oxidative stress on the host, but also that replication of the virus requires oxidative conditions for viral DNA transcription and virus maturation. Rickettsiales-like organisms are evolutionarily related to mitochondria, and therefore would be expected to have an oxidative metabolism that produces free radicals, which may explain the tropism for red blood cells which have high levels of glycolysis products, which serve as substrates for oxidative respiration, high levels of oxygen, and a reservoir of glutathione which detoxify free radicals.

The Rickettsiales-like organisms may produce, as a metabolic product, superoxide radical, which can induce oxidative and free radical damage within the RBC, as well as cause ancillary oxidative stress on other organs, such as the liver and lymphocytes.

It has further been found that a low frequency electromagnetic signal is associated with the DNA of the RBC fraction of HIV-infected individuals and not in non-infected individuals, and also not in the 400 bp sequence in a long-term HIV non-progressor (an HIV infected individual who appears to have a natural ability to suppress progression of the HIV infection). This finding might be explained by the fact that the rickettsiales-like organism within an HIV-infected host, including the 400 bp associated sequence, selectively generates free radicals and oxidative stress; these interact with the DNA within the RBC, to generate relatively stable structures that resonate at low frequencies and are thus detectable. The 400 bp associated sequences may, for example, suppress an antioxidant process of the rickettsiales-like organism, thus leading to an increased oxidative environment as compared to rickettsiales-like organisms that do not include the 400 bp associated sequence.

The absence of signal in a non-progressor patient may be due to an immune response of that individual that suppresses the HIV induction of the enhanced oxidative stress, even in the presence of the 400 bp associated sequence.

The RBCs typically have a high concentration of reduced glutathione, so that in an HIV-negative host, the signal is not generated. On the other hand, HIV-infected individuals (other than the non-progressor) have an oxidative stress that reduces glutathione levels in the erythrocytes, and thus permits interaction of the free radicals or other oxidative chemical species with the DNA. This interaction can result in a resonance that is externally measurable by an apparatus, e.g., US Pat. Pub. 2013/0143205, 2013/0217000, 2012/0024701, 2011/0076710, 2011/0027774, 2010/0323391, each of which is expressly incorporated herein by reference in its entirety.

The apparent eradication of this new agent can be achieved by a complementary treatment of HIV infection, according to the following protocol:

1) HIV infected patients are maintained under ARV treatment until undetectable viral load (<40 copies/ml) in their blood.

2) In addition they receive a strong antibiotic treatment for at least 15 days: 300 mg/day of doxycycline+2×500 mg of ciprofloxacin per day.

If the treatment is well tolerated, it could be further extended, e.g., by several weeks. Other antibiotics, such as narrow spectrum drugs, e.g., ebselen, ebsulfur and related drugs, might also be employed in the therapy. See, WO2007/137255, expressly incorporated herein by reference it its entirety.

If a Herxheimer reaction (also known as the Jarisch-Herxheimer reaction) is observed (fever, fatigue), due to an excess release of microbial antigens by the antibiotic treatment, this antibiotic treatment should be reduced or temporarily stopped until the symptoms disappear.

The goal of this antibiotic treatment is to reduce or even abolish the presence of the microbial factor in red blood cells (RBC): this is assessed by the PCR measurements in RBC using:

a) the primers for 16S ribosomal Rickettsiales DNA;
b) the primers for 214 and 237 bp of chromosomes 7 & 1; and/or
c) the primer of 400 bp of chr. 1 (400 bp plus 16S preferred).

The characteristic DNA bands should have decreased by 90%, as measured by quantitative real time PCR. If this reduction is not achieved, a second course of antibiotics should be administered, after a 3 week pause.

3) An antioxidant treatment is given, when the 90% reduction is attained, as follows:

a) Fermented *papaya* extract (FPP, Osato Research Institute, Japan) 3 sachets of 3 g/day for 3 months;
b) Glutathione/vitamin C "Thyogen®", Health Maintenance Programs Inc. Elmsford, N.Y., 4 capsules of each 1 gram/day between meals for 3 months. (Start progressively and ramp up to this dose).

Measurements of reduced and oxidized glutathione may be performed before and after treatment.

4) If the antibiotic treatment has not been able to decrease significantly the microbial infection, a third course of (possibly different) antibiotics may be necessary.

But, if the results of treatment 2 (antibiotics) show a significant decrease of the RBC DNA and if the results of treatment 3 (antioxidants) show a significant decrease of oxidative stress, (reduced glutathione back to normal rates), this means that these combined treatments have been able to decrease significantly the microbial infection.

Then one may be justified to discontinue the ARV treatment for one month, a procedure generally considered as harmless for the patient, provided that the ARV treatment is resumed in case of virus load rebound during this period.

The ultimate goal will be achieved when there will be no rebound of the HIV virus upon long term discontinuation of the ARV treatment. The use of immunostimulants (Gc-MAF, combination of cytokines) is also possible for attaining this objective.

Thus, with the help of a restored immune system, a functional eradication of HIV infection will be close.

REFERENCES

Each of the Following is Expressly Incorporated by Reference in its Entirety

1. L. Montagnier, J. Aissa, C. Lavallee, M. Mbamy, J. Varon, and H. Chenal, "Electromagnetic detection of HIV DNA in the blood of AIDS patients treated by antiretroviral therapy", Interdiscip Sci Comput Life Sci. 1:245-253 (2009).
2. Luc Montagnier, Rene Olivier, Catherine Pasquier; Oxidative Stress in Cancer, AIDS, and Neurodegenerative Diseases (Oxidative Stress and Disease), CRC Press (1997).
3. Awodele, Olufunsho, Sunday O. Olayemi, Joseph A. Nwite, and Titilope A. Adeyemo. "Investigation of the levels of oxidative stress parameters in HIV and HIV-TB co-infected patients." *The Journal of Infection in Developing Countries* 6, no. 01, pp 79-85 (2011).
4. Peden, K., Emerman, M., Montagnier, L. "Changes in growth properties on passage in tissue culture of viruses derived from infectious molecular clones of HIV-1LAI, HIV-1MAL, and HIV-1ELI", Virology 185, 661-672 (1991).
5. Gillespie, Joseph J., Brayton, Kelly A., Williams, Kelly P., Quevedo Diaz, Marco A., Brown, Wendy C., Azad, Abdu F., and Sobral, Bruno W., "Phylogenomics Reveals a Diverse Rickettsiales Type IV Secretion System", Infect Immun.; 78(5): 1809-1823 (2010).

What is claimed is:

1. A method of detecting presence of an intracellular organism in human erythrocytes having a nucleic acid which when present, is selectively associated with HIV infection, the intracellular organism having at least one DNA sequence which is adapted to be amplified by performing PCR on nucleic acids from enucleated erythrocytes, with primers comprising:

```
5'-CCT GAG AAG AGA TTT AAG AAC AAA;  SEQ ID NO: 001
and

5'-CCA TAT ACT GCT TCT ARY TGC T,    SEQ ID NO: 002
``` the method comprising:
collecting a specimen comprising erythrocytes from a human;
extracting DNA from within the erythrocytes;
selectively amplifying the nucleic acid if present in the extracted DNA; and
detecting an amplicon corresponding to the nucleic acid.

2. The method according to claim 1, wherein a presence of an amplicon indicates coinfection with HIV and a rickettsiales-like organism.

3. The method according to claim 1, further comprising treating a patient having HIV infection, which produces an amplicon from said PCR, with at least one antibiotic, until a PCR amplicon from PCR with the at least one primer is substantially diminished.

4. The method according to claim 3, wherein the at least one antibiotic comprises a tetracycline class antibiotic targeting 16S RNA of an organism having an amplicon from PCR with the at least one primer.

5. The method according to claim 3, wherein the at least the antibiotic comprises a fluoroquinolone class antibiotic.

6. The method according to claim 3, further comprising administering at least one immunostimulant and at least one antioxidant sufficient to increase glutathione levels in human erythrocytes, to induce a Th1 immune response pattern, after the PCR amplicon from PCR with the at least one primer is substantially diminished.

7. The method according to claim 6, wherein the at least one antioxidant comprises orally administered glutathione.

8. The method according to claim 6, wherein the immunostimulant is selected from the group consisting of at least one of a microbial product, a botanical extract, and a cytokine.

9. A method of detecting an intracellular microbe within human erythrocytes, comprising extracting DNA from the human erythrocytes, performing PCR with primers comprising:

```
5'-CCT GAG AAG AGA TTT AAG AAC AAA,  SEQ ID NO: 001
and

5'-CCA TAT ACT GCT TCT ARY TGC T;    SEQ ID NO: 002
``` and
detecting an amplicon associated with the PCR.

10. The method according to claim 9, wherein the amplicon comprises a 16S ribosomal RNA.

11. The method according to claim 9, further comprising selectively administering at least one antibiotic to a human from which the human erythrocytes originate, selectively dependent on said detection of the amplicon.

12. The method according to claim 11, further comprising continuing the administering of the at least one antibiotic until the amplicon is diminished, and subsequently administering at least one immunostimulant and at least one antioxidant.

13. The method according to claim 11, wherein the at least one antibiotic is adapted to suppress growth of at least one microorganism selected from the group consisting of an alpha-proteobacteria, a gamma-proteobacteria, and a rickettsiales-like organism.

14. The method according to claim 11, wherein the at least one antibiotic comprises a tetracycline class antibiotic.

15. The method according to claim 11, wherein the at least one antibiotic comprises a fluoroquinolone class antibiotic.

16. The method according to claim 11, further comprising concurrently administering an antiretroviral therapy effective for treatment of HIV infection.

17. The method according to claim 11, wherein the intracellular microbe has a 16S RNA homologous with at least one alpha- or gamma-proteobacterial organism, the human from which the human erythrocyte is obtained is infected with HIV, further comprising concurrently administering an immunostimulant therapy and an antioxidant therapy in an effective dose to delay detectability of HIV replication in the human by PCR of blood plasma.

18. A method of detecting microbial DNA associated with enucleated human erythrocytes, comprising:
extracting DNA from the enucleated human erythrocytes;
performing PCR with primers comprising:

```
5'-CCT GAG AAG AGA TTT AAG AAC AAA,SEQ ID NO: 001
and

5'-CCA TAT ACT GCT TCT ARY TGC T;   SEQ ID NO: 002
``` and
detecting an amplicon from the PCR.

19. The method according to claim 18, further comprising employing PCR to detect at least a portion of HIV LTR in plasma from a patient from which the enucleated human erythrocytes are derived.

* * * * *